US005468752A

United States Patent [19]
Freeman

[11] Patent Number: 5,468,752
[45] Date of Patent: Nov. 21, 1995

[54] TREATMENT OF CONDITIONS OF ABNORMALLY INCREASED INTRAOCULAR PRESSURE BY ADMINISTRATION OF HPMPC AND RELATED PHOSPHONYLMETHOXYALKYLCYTOSINES

[76] Inventor: William R. Freeman, 2361 Lozana St., Del Mar, Calif. 92014

[21] Appl. No.: 222,128

[22] Filed: Apr. 4, 1994

[51] Int. Cl.⁶ .................................................. A61K 31/505
[52] U.S. Cl. .......................................... 514/272; 514/912
[58] Field of Search ..................................... 514/272, 913

[56] References Cited

U.S. PATENT DOCUMENTS

| | | | |
|---|---|---|---|
| 4,230,708 | 10/1980 | De Clercq et al. | 424/253 |
| 4,605,658 | 8/1986 | Holy et al. | 514/261 |
| 4,724,233 | 2/1988 | De Clercq et al. | 514/81 |
| 5,142,051 | 8/1992 | Holy et al. | 544/243 |

OTHER PUBLICATIONS

Chemical Abstract 119: 151515 (1993). Clercq.
Andrei, et al., "Comparative Activity of Selected Antiviral Compounds against Clinical Isolates of Human Cytomagalovirus," *Eur. J. Clin. Microbiol. Infect. Dis.* 10(12):1026–1033 (1991).
Cantrill, et al., "Treatment of Cytomegalovirus Retinitis with Intravitreal Ganciclovir," *Ophthalmology* 96(3):367–374 (1989).
Erik De Clercq, "Broad–Spectrum Anti–DNA Virus and Anti–Retrovirus Activity of Phosphonylmethoxyalkylpurines and —Pyrimidines," *Biochem. Pharm.* 42(5):963–972 (1991).
William R. Freeman, "Intraocular Antiviral Therapy," *Arch. Ophthalmol.* 107:1737–1739 (1989).
Friberg and Paul, "CMV Retinitis and Immunosuppression with FK506," *Retina/Anatomy & Pathology/Clinical Res./Immunology & Microbiology Paper Presentation* 291:11:15 (Abstract), Investigative Ophthalmology & Visual Science, Annual Meeting Abstract Issue, May 3–8, 1992, Sarasota, Fla.
Freeman, et al., "HPMPC for the Long Acting Treatment of Experimental Herpes Simplex Retinitis in Rabbits," 292:11:30 (Abstract), Investigative Ophthalmology & Visual Science, Annual Meeting Abstract Issue, May 3–8, 1992, Sarasota, Fla.
Gross, et al., "Longitudinal Study of Cytomegalovirus Retinitis in Acquired Immune Deficiency Syndrome," *Ophthalmology* 97:681–686 (1990).
Henderly, et al., "Cytomegalovirus Retinitis and Response to Therapy With Ganciclovir," *Ophthalmology* 94(4):425–434 (1987).
Henry, et al., "Use of Intravitreal Ganciclovir (Dihydroxy Propoxymethyl Guanine) for Cytomegalovirus Retinitis in a Patient With AIDS," *Am. J. Ophthal.* 103(1):17–23 (1987).
Douglas A. Jabs, "Treatment of Cytomegalovirus Retinitis–1992," *Arch. Ophthalmol.* 110:185–187 (1992).
Maudgal and De Clercq, "(S)-1-(3-Hydroxy-2-Phosphonyl-Methoxypropyl)Cytosine in the Therapy of Thymidine Kinase-Positive and –Deficient Herpes Simplex Virus Experimental Keratitis," *Investigative Ophthalmol. & Visual Sci.* 32(6):1816–1820 (1991).
Neyts, et al., "Selective Inhibition of Human Cytomegalovirus DNA Synthesis by (S)—1—(3—Hydroxy—2—phosphonylmethoxypropyl)cytosine [(S)—HPMPC] and 9—(1, 3—Dihydroxy—2—propoxymethyl)guanine (DHPG)," *Virology* 179:41–50 (1990).
Neyts, et al., "Efficacy of (S)—1—(3—Hydroxy—2—Phosphonylmethoxypropyl)Cytosine and 9—(1,3—Dihydroxy—2—Propoxymethyl)Guanine for the Treatment of Murine Cytomegalovirus Infection in Severe Combined Immunodeficiency Mice," *J. Med. Virol.* 37:67–71 (1992).
Sanborn, et al., "Substained–Release Ganciclovir Therapy for Treatment of Cytomegalovirus Retinitis," *Arch. Ophthalmol.* 110:118–195 (1992).
Smith, et al., "Intravitreal Sustained–Release Ganciclovir," *Arch. Opthalmol.* 110:225–258 (1992).
Ussery, et al., "Intravitreal Ganciclovir in the Treatment of AIDS–associated Cytomegalovirus Retinitis," *Ophthalmology* 95(5):640–648 (1988).
Andreoli, et al., editors, *Cecil Essentials of Medicine* W.B. Saunders Company, publishers, pp. 690–691 (1986).
Leibrandt, editor, *Professional Guide to Disease*, pp. 1203–1206 (1982).
Berthe, et al., "Toxicologic and Pharmacokinetic Analysis of Intravitreal Injections of Foscarnet, Either Alone or in Combination With Ganciclovir," *Invest. Ophthal. & Visual Sci.* 35(3):1038–1045 (1994).
De Clercq, Erik, "Antivirals for the treatment of herpesvirus Infections," *J. Antimicrobial Chemotherapy* 32(A):121–132 (1993).
Diaz–Llopis, et al., "Intravitreal Foscarnet for Cytomegalovirus Retinitis in a Patient With Acquired Immunodefi (List continued on next page.)

Primary Examiner—Zohreh Fay
Attorney, Agent, or Firm—Stephanie L. Seidman; Brown, Martin, Haller & McClain

[57] ABSTRACT

Treatment of conditions of abnormally increased intraocular pressure, particularly those caused by glaucoma, by administration of a phosphonylmethoxypropyl cytosine compound, preferably (S)-1-(3-hydroxy-2-phosphonyl-methoxypropyl) cytosine [HPMPC], is disclosed. The cytosine compounds may be present preferably as a free drug or alternatively encapsulated into liposomes or other :long acting drug delivery systems, Administration of the compound may be by intravitreal injection, aqueous humor injection, injection into the external layers of the eye, such as subconjunctival injection or subtenon injection, or by topical drops, in an inert carrier. The degree of reduction in pressure is dosage-dependent, and significant reduction in pressure is obtained. A single injection is expected to be sufficient to produced prolonged, and perhaps permanent, lowering of the intraocular pressure, although in some cases additional injections may be required at infrequent intervals. The amount of the compound administered may be varied by the physician to obtain the desired degree of pressure decrease. Also disclosed are the compositions used in the method.

19 Claims, No Drawings

OTHER PUBLICATIONS ciency Syndrome," *American J. of Ophthalmology* 115(5):686–688 (1993).

Li, et al., "Activity of (S)—1—(3—hydroxy—2—phosphonylmethoxypropyl)cytosine (HPMPC) against guinea pig cytomegalovirus infection in cultured cells and in guinea pigs," *Antiviral Research* 13:237–252 (1990).

Saffar, et al., "Transscleral Iontophoresis of Foscarnet," *American J. of Ophthalmology* 115:748–754 (1993).

Neyts, et al., "Efficacy of (S)—1—(3—Hydroxy—2—Phosphonylmethoxypropyl)Cytosine and 9—(1,3—Dihydroxy—2—Propoxymethyl)Guanine for the Treatment of Murine Cytomegalovirus Infection in Severe Combined Immunodeficiency Mice," *J. of Medical Virology* 37:67–71 (1992).

Shigeta, et al., "Comparative Inhibitory Effects of Nucleoside Analogues on Different Clinical Isolates of Human Cytomegalovirus in Vitro," *J. of Infectious Diseases* 163:270–275 (1991).

TREATMENT OF CONDITIONS OF ABNORMALLY INCREASED INTRAOCULAR PRESSURE BY ADMINISTRATION OF HPMPC AND RELATED PHOSPHONYLMETHOXYALKYLCYTOSINES

BACKGROUND OF THE INVENTION

1. Field of the invention

The invention herein relates to the treatment of glaucoma and other conditions of abnormally increased intraocular pressure. More particularly it relates to treatment by application of therapeutic compounds.

2. Description of the Prior Art

Glaucoma, the abnormally increased level of intraocular pressure, is one of the leading causes of blindness in the United States. Glaucoma has several related forms, but all involve the abnormal increase in intraocular pressure primarily by obstruction of the outflow of aqueous humor from the eye, or, less frequently, by overproduction of aqueous humor within the eye. Glaucoma in its various forms is widely described in the literature: see, e.g., Leibrandt, ed., Professional Guide to Diseases, 1203–1206 (1982) and Andreoli et al, eds., Cecil: Essentials of Medicine, 690–691 (1986). Glaucoma is primarily diagnosed by Schiøtz or applanation tonometry, with gonioscopy, ophthalmoscopy, slit-lamp examination, fingertip tension and perimetry or visual field tests also being useful as diagnostic methods.

In the past treatment has involved administration of beta-blockers such as timolol to decrease aqueous humor production, epinephrine to lower intraocular pressure or diuretics such as acetazolamide, or administration of miotic eyedrops such as pilocarpine to facilitate the outflow of vitreous humor. Acute forms of glaucoma may require peripheral iridectomy surgery to relieve pressure where drug therapy is ineffective and the patient's vision is at immediate risk. Other forms of treatment have included physical or thermal destruction ("cyclo-destruction") of the ciliary body of the eye, commonly by surgery or application of a laser beam, cryogenic fluid or high frequency ultrasound. Each of these methods of destruction is costly and unduly invasive (S)-1-(3-hydroxy-2-phosphonyl-methoxypropyl) cytosine [HPMPC], a phosphonylmethoxypropyl cytosine compound, is described in Maudgal et al., Invest. Ophthalmol. and Visual Sci., 32(6): 1816–1820 (1991). Descriptions of the use and efficacy of HPMPC with respect to treatment of viral diseases are described in Maudgal et al., supra; Neyts et al., Virology, 179(1): 41–50 (1990) and Andrei et al., Eur. J. Clin. Microbiol. Infect. Dis., 10(12): 1026–1033 (1991). Glaucoma, however, is not a viral condition, and therefore the treatments for the viral eye diseases discussed in the prior art have heretofore not been believed to be applicable to treatment of glaucoma.

SUMMARY OF THE INVENTION

In its broadest aspects, the invention comprises the treatment of glaucoma by administration of a phosphonylmethoxypropyl cytosine compound, preferably (S)-1-(3-hydroxy-2-phosphonyl-methoxypropyl) cytosine [HPMPC], preferably as a free drug or, alternatively, encapsulated into liposomes or other long acting drug delivery systems, and the injectable or topical compositions used in the method. The method produces significant and long term lowering of intraocular pressure, commonly down to at least 3–7 mm Hg and in some cases down essentially to 0 mm Hg.

Thus, one aspect is a method for the treatment of glaucoma which comprises administering an effective amount of a phosphonylmethoxypropyl cytosine compound (preferably HPMPC) in an amount in the range of 1–1000 µg/ml, preferably 10–200 µg/ml, more preferably 20–200 µg/ml, of vitreous. Administration of the compound may be by intravitreal injection, aqueous humor injection, injection into the external layers of the eye, such as subconjunctival injection or subtenon injection, or by topical drops, in an inert carrier. It is believed that a single injection will be sufficient to produced prolonged, and perhaps permanent, lowering of the intraocular pressure, although in some cases additional injections may be required at infrequent intervals. The amount of the compound administered maybe varied by the physician to obtain the desired degree of pressure decrease.

Another aspect is a composition for the treatment of glaucoma which comprises a phosphonylmethoxypropyl cytosine compound in a therapeutically effective amount in a dosage range of 1–1000 µg/ml, preferably 10–200 µg/ml, more preferably 20–200 µg/ml, of vitreous, in an inert carrier.

DETAILED DESCRIPTION AND PREFERRED EMBODIMENTS

This invention comprises the administration of the antiviral compound (S)-1-(3-hydroxy-2-phosphonyl-methoxypropyl) cytosine [HPMPC] and its cytosine analogs by intravitreal injection, aqueous humor injection, injection into the external layers of the eye, such as subconjunctival injection or subtenon injection, or by topical drops, preferably in free form but alternatively in liposomes or other sustained drug delivery devices, for the direct, local therapy of glaucoma. The applicability and efficacy of this type of antiviral drug is unexpected and surprising, since glaucoma is not a viral disease nor are its various manifestations significantly affected by viral conditions of the patient. Administration of the compound is preferably by intravitreal injection. Administration by topical drops, while the least invasive for the patient, may in some cases fail to deliver a sufficient quantity of the compound to the eye. The routes of administration, especially by injection, are specialized and unique and the properties of the compound which make it so highly suitable for this use include its lack of toxicity (other than to decrease aqueous secretion), high intraocular therapeutic index, optical clarity which precludes it from adversely affecting the vision of the eye to which it is administered, and its high water solubility which allows extremely small volumes to be injected under topical or local anesthetics into the mid-vitreous cavity of the human eye, preferably through self sealing 25–30 gauge needles.

An additional unexpected and surprising aspect of this therapy method is the apparent ability of a single intravitreal injection of the administered HPMPC to provide substantial and long lasting reduction in intraocular pressure. Reductions to at least a modest 3–7 mm Hg are possible (8–22 mm Hg is the normal pressure range) and in some cases the level of essentially 0 mm Hg has been reached and maintained. By another measure, reductions in the amount of at least 20 mm Hg can usually be obtained. It appears that in many cases a single intravitreal injection may be sufficient to obtain permanent reduction. Even where the reduction is not permanent, it is expected that further injections will be required only on an infrequent basis.

This property is totally unexpected since prior studies have indicated that the duration of efficacy of HPMPC for treatment of viral diseases is only a few days. While the mechanism of this surprisingly extended or possibly permanent period of efficacy for the treatment of the non-viral glaucoma by injection or topical administration is not fully understood, it is believed that it is because of the ability of the compounds as so administered to decrease the ability of the ciliary body of the eye to secrete aqueous humor. The ciliary body is preferably accessed by intravitreal injection or by aqueous humor injection. Alternatively, administration by injection into the external layers of the eye, such as subconjunctival injection or subtenon injection, is expected to result in significant levels of the drug within the aqueous or vitreous fluids which would then gain access to the ciliary body. It is anticipated that topical administration should have a similar effect, although whether topical administration will yield sufficiently high aqueous levels in all cases remains to be tested.

HPMPC is polar and highly water soluble and is well suited to ocular use, especially in this invention where intraocular injection is the preferred method of administration. The methods of drug delivery are determined by the recognition that the eye is a self contained, closed system. An unexpected and surprising effect of this use of HPMPC has been found to be the non-toxic nature of even high doses of HPMPC when directly injected into the vitreous allowing the retina to be directly bathed in drug concentrations of 1–1000 µg/ml, preferably 10–200 µg/ml, more preferably 20–200 µg/ml, of vitreous. (Dosages of HPMPC will normally be stated herein on a microgram of HPMPC per milliliter of vitreous (µg/ml) basis. Unless otherwise noted, the quantity of carrier-plus-HPMPC—"drug"—normally administered was 0.1 ml.) This is the equivalent of an intravitreal therapeutic index of HPMPC for glaucoma of 1000:1 or greater.

The HPMPC as dissolved in an inert clear carrier drug is itself optically clear and can be filter sterilized using nylon 66 matrix 0.22 µm sterile syringe filter systems that cause no ocular toxicity. Injection into the eye may be through the pars plana via a self-sealing needle (preferably 25–30 gauge). While it is preferred to use the free drug, it is also possible to incorporate the drug into sustained release vehicles. For instance, HPMPC and its analogs may be encapsulated at high efficiency into the aqueous phase of liposome systems which I have found to be non toxic to the eye.

In an experimental study of this method, twenty patients having normal intraocular pressure but suffering from CMV retinitis were each injected into the vitreous cavity with HPMPC in an amount of 10–100 µg in total volume of 0.1 ml. The pressure lowering effect began within 3–14 days and was observed to be long lasting. The degree of pressure reduction depended on the dosage, with the lowest dosages (~10 µg/ml of vitreous) producing relatively small amounts of pressure reduction, the largest (~100 µg/ml of vitreous) producing the maximum reduction (in some cases down to essentially 0 mm Hg), and the intermediate dosages producing intermediate degrees of pressure reduction.

In another study, the effect of reduction of intraocular pressure has been shown in guinea pigs at doses that give intravitreal levels of HPMPC on the order of 100 µg/ml of vitreous. Histologic studies of the guinea pigs show changes in the structure of the ciliary body which would be expected to lower aqueous secretion. It appears, however, that the pressure reduction effect of HPMPC may be species-specific, in that the effect has not been observed in tests with rabbits, micro-mini pigs, or Papiao cynocephalus monkeys, even at higher dosages.

Optical properties of the compound when injected into the vitreous cavity were assessed by indirect ophthalmoscopy and fundus photography as well as by observing the behavioral characteristics of the animals who underwent intravitreal injection. In all cases, the optical pathways were normal as was animal visual behavior indicating that the compound does not obstruct or affect the visual pathways in any way. This indicates that the intravitreal injection of the compound as described would result in no adverse effects and will have a major therapeutic effect.

It will be evident that there are numerous other embodiments of the protocols, techniques, methods and materials described which, while not expressly set forth above, are clearly within the scope and spirit of the invention. The above description is therefore to be considered exemplary only, and the actual scope of the invention is to be determined solely by the appended claims.

I claim:

1. A method for the treatment of abnormally increased intraocular pressure which comprises administering a therapeutically effective amount of a phosphonyl-methoxypropyl cytosine compound.

2. A method as in claim 1 wherein said cytosine compound is administered in an amount in the range of 1–1000 micrograms per milliliter of vitreous.

3. A method as in claim 2 wherein said cytosine compound is administered in an amount in the range of 10–200 micrograms per milliliter of vitreous.

4. A method as in claim 3 wherein said cytosine compound is administered in an amount in the range of 20–200 micrograms per milliliter of vitreous.

5. A method as in claim 1 wherein said cytosine compound is (S)-1-( 3-hydroxy-2-phosphonyl-methoxypropyl) cytosine.

6. A method as in claim 5 wherein said (S)-1-(3-hydroxy-2-phosphonyl-methoxypropyl) cytosine is administered in an amount in the range of 1–1000 micrograms per milliliter of vitreous.

7. A method as in claim 6 wherein said (S)-1-(3-hydroxy-2-phosphonyl-methoxypropyl) cytosine is administered in an amount in the range of 10–200 micrograms per milliliter of vitreous.

8. A method as in claim 7 wherein said (S)-1-(3-hydroxy-2-phosphonyl-methoxypropyl) cytosine is administered in an amount in the range of 20–200 micrograms per milliliter of vitreous.

9. A method as in claim 1 wherein said cytosine compound is in the form of a free drug.

10. A method as in claim 1 wherein administration of said compound comprises intravitreal injection, aqueous humor injection, injection into the external layers of the eye or topical administration.

11. A method as in claim 10 wherein said administration comprises a single injection.

12. A method as in claim 10 wherein said administration comprises a plurality of injections administered at infrequent 13. A method as in claim 10 wherein said cytosine compound is (S)-1-( 3-hydroxy-2-phosphonyl-methoxypropyl) cytosine.

14. A method as in claim 13 wherein said cytosine compound is in the form of a free drug.

15. A method as in claim 13 wherein said cytosine compound is encapsulated into liposomes.

16. A method as in claim 1 wherein the condition of abnormally increased intraocular pressure comprises glaucoma.

17. A method as in claim 5 wherein the condition of abnormally increased intraocular pressure comprises glaucoma.

18. The method of claim 1, wherein the amount administered is about 10–100 µg.

19. The method of claim 5, wherein the amount administered is about 10–100 µg.

* * * * *